(12) United States Patent
Stauffer

(10) Patent No.: US 6,545,191 B1
(45) Date of Patent: Apr. 8, 2003

(54) PROCESS FOR PREPARING ETHANOL

(76) Inventor: John E. Stauffer, 6 Pecksland Rd., Greenwich, CT (US) 06831

( * ) Notice: Subject to any disclaimer, the term of this patent is extended or adjusted under 35 U.S.C. 154(b) by 0 days.

(21) Appl. No.: 10/171,361

(22) Filed: Jun. 13, 2002

(51) Int. Cl.$^7$ .......................... C07C 27/00; C07C 29/00
(52) U.S. Cl. ....................................... 568/893; 568/894
(58) Field of Search ................................. 568/893, 894

(56) References Cited

U.S. PATENT DOCUMENTS

| | | | |
|---|---|---|---|
| 4,990,696 A | | 2/1991 | Stauffer |
| 5,097,083 A | * | 3/1992 | Stauffer ...................... 570/241 |
| 5,185,479 A | | 2/1993 | Stauffer |
| 6,137,017 A | * | 10/2000 | Stauffer ...................... 568/893 |

OTHER PUBLICATIONS

Selim M. Senkan, Converting Methane by Chlorine–Catalyzed Oxidative Pyrolysis, Dec., 1987, *Chemical Engineering Progress*.

* cited by examiner

*Primary Examiner*—Johann Richter
*Assistant Examiner*—Elvis O. Price
(74) *Attorney, Agent, or Firm*—Young & Basile, P.C.

(57) ABSTRACT

The specification discloses a process for the production of ethyl alcohol (ethanol), the process comprising first and second reaction steps operated in tandem. In the first reaction step, ethyl chloride, hydrogen chloride, perchloroethylene and oxygen are reacted in the presence of a catalyst, using ethane as a diluent, to yield reaction products comprising ethyl alcohol and hexachloroethane. Substantially all of the oxygen and hydrogen chloride reactants of this first reaction step are consumed. The ethyl alcohol is isolated from these reaction products. In the second reaction step, the hexachloroethane from the first reaction step is reacted with ethane to produce the ethyl chloride, hydrogen chloride, and perchloroethylene used as reactants in the first reaction step. These reaction products are supplied to the first reaction step, along with any unreacted ethane.

9 Claims, 1 Drawing Sheet

PROCESS FOR PREPARING ETHANOL

FIELD OF THE INVENTION

The present invention relates to a process of producing ethyl alcohol (ethanol), and more particularly to such a process where ethyl chloride, hydrogen chloride, perchloroethylene and oxygen are reacted in the presence of a catalyst, using ethane as a diluent, to yield reaction products comprising ethyl alcohol and hexachloroethane, and wherein the hexachloroethane is reacted with ethane to produce the ethyl chloride, hydrogen chloride, and perchloroethylene reactants for the ethyl alcohol and hexachloroethane producing reaction.

BACKGROUND OF THE INVENTION

Ethyl alcohol is a chemical compound having a multitude of industrial and commercial applications, including as a precursor in the production of numerous organic chemicals such as ether, butadiene, chloroform, as well as in the production of beverage alcohols, and as a fuel for internal combustion engines.

Ethanol is conventionally manufactured for industrial uses by one of the following two methodologies. According to the first method, ethtylene is hydrolyzed under various conditions to form ethyl alcohol. Per the second method, which dates back centuries, ethyl alcohol is produced by the fermentation of sugar with yeast. Ethanol used for alcoholic beverages is produced almost exclusively by this fermentation process. Although practiced on a large scale, both of the foregoing methods suffer drawbacks, including relatively high production costs. For example, ethylene, the ethanol precursor in the first method, is an expensive compound.

As disclosed in U.S. Pat. No. 5,185,479, issued to the named inventor hereof, it is known to produce methyl alcohol (methanol) by reacting perchloroethylene and methyl chloride with hydrogen chloride and air. This process, however, is attended by several operational drawbacks. When air is employed for oxychlorination, a substantial quantity of gases must be vented, thereby complicating emission control problems and related environmental concerns. On the other hand, the use of pure oxygen, as has been discovered by the inventor hereof, complicates the oxychlorination reaction due to the formation of hot spots on the catalyst. A further drawback is the need to employ an absorber/stripper facility in order to separate methane from hydrogen chloride in the effluent from the chlorination or thermal reactor. This requirement impacts the energy efficiency of the process, and further increases the capital investment necessary to produce methanol by this methodology.

There consequently exists a need for a process of manufacturing ethanol which is at once economical and reduces the inefficiencies characterizing conventional processes.

SUMMARY OF THE DISCLOSURE

The specification discloses a largely self-contained process for producing ethyl alcohol, comprising the following reaction steps, operated in tandem:

A first reaction step wherein ethyl chloride, hydrogen chloride, perchloroethylene and oxygen are reacted in the presence of a catalyst, using ethane as a diluent, to yield reaction products comprising ethyl alcohol and hexachloroethane; and a second reaction step wherein the hexachloroethane of the first reaction step is reacted with ethane to produce ethyl chloride, hydrogen chloride, and perchloroethylene, which products are supplied as reactants to the first reaction step, along with any unreacted ethane. Substantially all of the oxygen and hydrogen chloride reactants in the first reaction step are consumed, thereby doing away with the need for an absorber/stripper facility.

Per another feature of this process, the catalyst of the first reaction step comprises copper chloride or an admixture of copper chloride and a salt selected from the group consisting of potassium chloride, iron chloride, cesium chloride, zinc chloride, lead chloride, and bismuth chloride.

According to another feature of the invention, the first reaction step is carried out at a temperature in the range of from approximately 200° Centigrade to approximately 375° Centigrade.

Per another feature, the first reaction step is carried out at a pressure in the range of from approximately 2 atm. to approximately 10 atm.

Per still another feature, the second reaction step is carried out at a temperature in the range of from approximately 400° Centigrade to approximately 700° Centigrade.

BRIEF DESCRIPTION OF THE DRAWINGS

The written description herein makes reference to the accompanying drawings, of which.

WRITTEN DESCRIPTION

Figure 1:
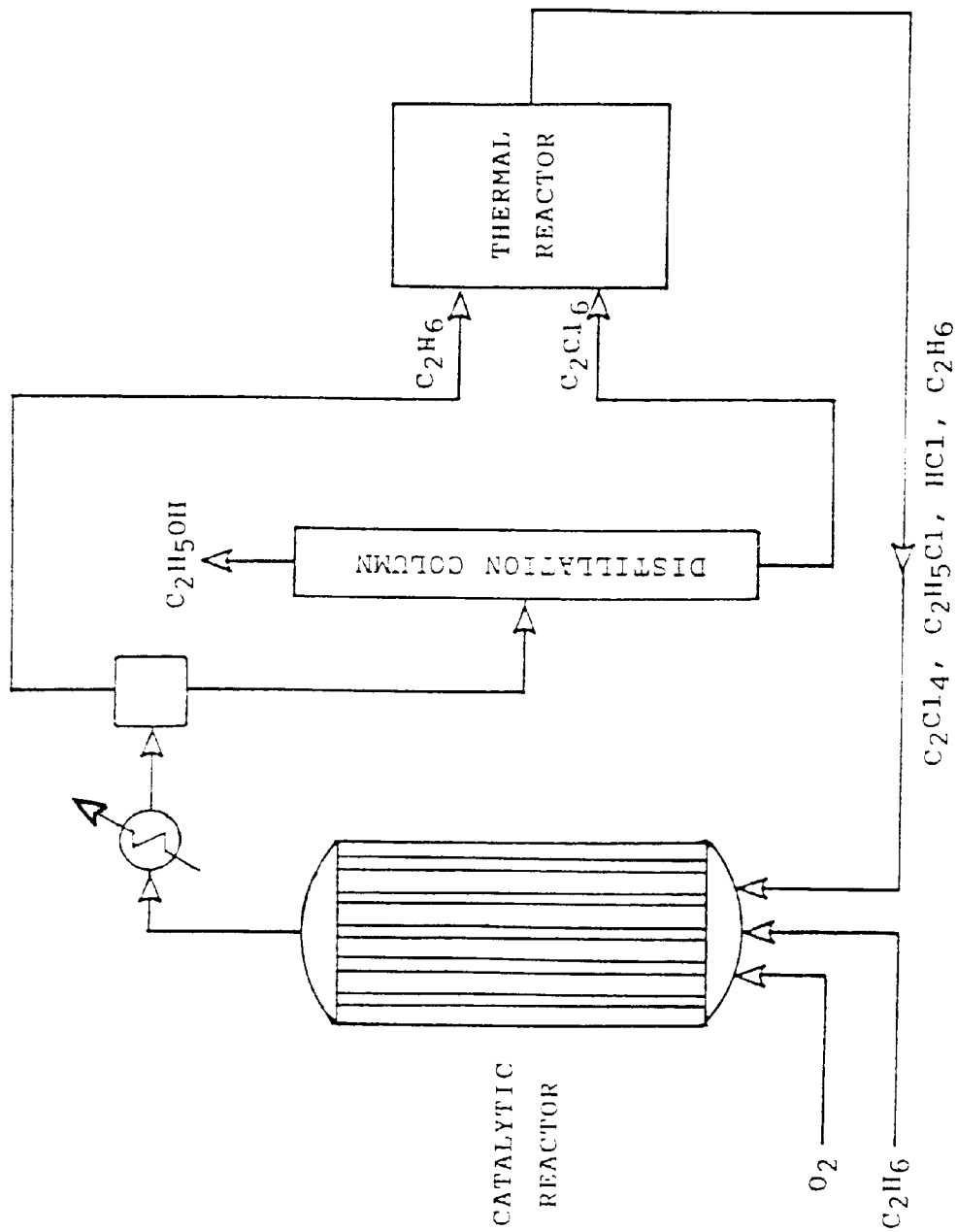
FIG. 1 is a flow diagram of the process of the present invention depicting two reactors, including a first catalytic reactor and a second thermal reactor, and a distillation column for separating the ethanol product.

Referring now to FIG. 1, wherein the process of this invention is shown diagrammatically, the present invention will be seen to essentially comprise a process for producing ethanol ($C_2H_5OH$) from oxygen ($O_2$) and ethane ($C_2H_6$). More particularly, the process of this invention comprises a first reaction step, wherein ethyl chloride ($C_2H_5Cl$), hydrogen chloride (HCl), perchloroethylene ($C_2Cl_4$) and oxygen are reacted in the presence of a catalyst, using ethane as a diluent, to give reaction products comprising ethyl alcohol and hexachloroethane ($C_2Cl_6$), and a second reaction step, wherein the hexachloroethane from the first reaction step is reacted with ethane to produce ethyl chloride, hydrogen chloride, and perchloroethylene, which products are supplied, along with any unreacted ethane, to the first reaction step.

The ethyl alcohol product is separated from the product stream of the first reaction step, for example by a distillation column.

These first and second reaction steps are represented, respectively, by the following equations (1) and (2):

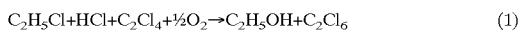

$$C_2H_5Cl + HCl + C_2Cl_4 + \tfrac{1}{2}O_2 \rightarrow C_2H_5OH + C_2Cl_6 \qquad (1)$$

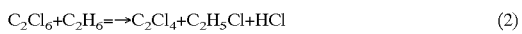

$$C_2Cl_6 + C_2H_6 = \rightarrow C_2Cl_4 + C_2H_5Cl + HCl \qquad (2)$$

The foregoing equations may be combined, as in the following equation (3), to represent the reaction of the present inventive process generally as the production of ethyl alcohol from oxygen and ethane, as described above:

$$C_2H_6 + \tfrac{1}{2}O_2 \rightarrow C_2H_5OH \qquad (3)$$

According to the first reaction step, shown in equation (1), ethyl chloride is hydrolyzed with water over a catalyst to produce ethyl alcohol and hydrogen chloride. This first reaction step, as shown in FIG. 1, is carried out in a catalytic reactor. The hydrogen chloride so formed is continually removed in situ by an oxychlorination reaction whereby perchloroethylene is converted to hexachloroethane. In this oxychlorination reaction, oxygen and hydrogen chloride are converted in the presence of a catalyst to water and chlorine. The chlorine reacts with the double bond in perchloroethylene. The water is consumed in the hydrolysis reaction. Consequently, the net reaction that takes place in the first reaction step is the conversion of ethyl chloride, hydrogen chloride, perchloroethylene and oxygen in the presence of a catalyst to ethyl alcohol and hexachloroethane.

To better appreciate the particulars of the inventive process, it is useful to have a knowledge of the bond dissociation energies of the relevant molecules. These data are disclosed in Senkan, "Converting Methane by Chlorine-Catalyzed Oxidative Pyrolysis," *Chemical Engineering Progress*, p. 58 (1987), the disclosure of which is incorporated herein by reference in its entirety. The bond-dissociation energy for the carbon-chloride (C—Cl) bond in ethyl chloride is 343 kJ/mole, from which it is apparent that, under the conditions of the first reaction step, shown in equation (1) above, the hydrolysis reaction will go to completion. Commensurate with this result, essentially all of the oxygen and hydrogen chloride in the feed to the catalytic reactor will be consumed. As such, the catalytic reactor effectively functions as a separator to strip hydrogen chloride from ethane.

Suitable catalysts for the oxychlorination reaction of the first reaction step comprise copper chloride or an admixture of copper chloride and a metal chloride selected from the group consisting of potassium chloride, iron chloride, zinc chloride, lead chloride, cesium chloride, and bismuth chloride. The oxychlorination catalyst may be deposited on an inert support for use in a shell and tube reactor or fluidized bed reactor. Alternatively, the catalyst may be in the form of a molten salt.

In the embodiment of the invention as described, the temperature for the first reaction step is in the range of from approximately 200° Centigrade to approximately 375° Centigrade.

The oxychlorination reaction is highly exothermic in nature. In contrast, the hydrolysis of ethyl alcohol is somewhat endothermic, a fact which tends to somewhat mitigate the heat generated by oxychlorination. The production of unwanted byproducts is further limited by the use of ethane as a diluent in the first reaction step. By carrying out the catalytic reaction of the first reaction step in the presence of ethane, which under the conditions of the reaction is inert and serves to remove beat from the catalyst surface, potentially troublesome hot spots in the catalyst are avoided.

The Law of Le Chatelier, which states that equilibrium tends to shift in such a way as to reduce changes in temperature, pressure and concentration, suggests that the first reaction step be conducted at elevated pressure. As shown in equation (1) above, 3.5 moles of reactants are converted to 2 moles of product so that increased pressure shifts the equilibrium in favor of the formation of product Elevated pressures also have the beneficial effects of improving heat transfer in the reactor and increasing the capacity of the apparatus. The upper limit of pressure may be determined by the increased cost of the reactor equipment. According to the embodiment of the process as described herein, the pressure of the first reaction step is in the range of 2 atm. to 10 atm.

In the second reaction step, ethane is reacted with the hexachloroethane product of the first reaction step to produce ethyl chloride, hydrogen chloride, and perchloroethylene for the first reaction step. This second reaction step, as shown in FIG. 1, is carried out in a thermal reactor. More particularly, the hexachloroethane decomposes to perchloroethylene and chlorine, and the chlorine in turn reacts with ethane to yield ethyl chloride and hydrogen chloride.

An excess of ethane is used in the chlorination of ethane in the second reaction step, equation (2) above, in order to suppress the formation of higher chlorinated compounds such as ethylene dichloride.

Without being bound to any particular theory, it is believed by the inventor that the probable mechanism by which ethane is chlorinated is a series of free-radical reactions.

Instead of being separated from hydrogen chloride in an absorber/stripper unit and recycled to the thermal reactor, any unreacted ethane from the thermal reactor is fed, along with the hydrogen chloride, ethyl chloride and perchloroethylene, to the catalytic reactor. Eventually this excess ethane will be returned to the thermal reactor because the exit stream from the catalytic reactor, after removal of the ethanol product, is introduced to the thermal reactor.

As indicated, the temperature for the first reaction step is in the range of from approximately 200° Centigrade to approximately 375° Centigrade. Because the bond dissociation energy for the carbon-hydrogen (C—H) bond in ethane is much greater than that for the C—Cl bond in ethyl chloride, the second reaction step is carried out at a considerably higher temperature, in the range of from approximately 400° Centigrade to approximately 700° Centigrade in the embodiment as described herein.

For the chlorination reaction of the second reaction step, pressures in the neighborhood of 1 atm. absolute are used in the thermal reactor.

The process as shown and described is largely a self-contained system Only oxygen and ethane are introduced, while only ethanol is removed. The process of this invention therefore beneficially minimizes environmental problems such as may be caused by the release of chlorinated organics. While some inert gases may build up in the system, these quantities will be small, and the gases may be purged by a vent (not shown in FIG. 1).

By operating the first and second reaction steps in conjunction in the same overall system, according to which products from the first reaction step are supplied to the second reaction step, and products from the second reaction step are, in turn, supplied to the first reaction step, there is no net consumption or production of hydrogen chloride and perchloroethylene. And because high yields are possible in both reaction steps, the overall efficiency of the process of this invention is high.

Moreover, the operation of the inventive process is made commercially quite practicable by the availability of oxygen in commercial quantities. And ethane, with its boiling point of −88.6° Centigrade, is relatively easily fractionated Of course, the foregoing is merely illustrative of the present invention. Those of ordinary skill in the art will appreciate that many additions and modifications to the present invention, as set out in this disclosure, are possible without departing from the spirit and broader aspects of this invention as defined in the appended claims.

The invention in which an exclusive property or privilege is claimed is defined as follows:

1. A process for producing ethyl alcohol, comprising the following reaction steps, operated in tandem:
   a first reaction step wherein ethyl chloride, hydrogen chloride, perchloroethylene and oxygen are reacted in the presence of a catalyst, using ethane as a diluent, to yield reaction products comprising ethyl alcohol and hexachloroethane;

a second reaction step wherein the hexachloroethane of the first reaction step is reacted with ethane to produce ethyl chloride, hydrogen chloride, and perchloroethylene, which products are supplied as reactants to the first reaction step, along with any unreacted ethane; and wherein substantially all of the oxygen and hydrogen chloride reactants in the first reaction step are consumed.

2. The process of claim 1, wherein the catalyst of the first reaction step comprises copper chloride.

3. The process of claim 1, wherein the catalyst of the first reaction step comprises an admixture of copper chloride and a salt selected from the group consisting of potassium chloride, iron chloride, cesium chloride, zinc chloride, lead chloride, and bismuth chloride.

4. The process of claim 1, wherein the first reaction step is carried out at a temperature in the range of from approximately 200° Centigrade to approximately 375° Centigrade.

5. The process of claim 1, wherein the second reaction step is carried out at a temperature in the range of from approximately 400° Centigrade to approximately 700° Centigrade.

6. The process of claim 1, wherein the first reaction step is carried out at a pressure in the range of from approximately 2 atm. to approximately 10 atm.

7. The process of claim 1, wherein the first reaction step is carried out at a temperature in the range of from approximately 200° Centigrade to approximately 375° Centigrade and at a pressure in the range of from approximately 2 atm. to approximately 10 atm., and the second reaction step is carried out at a temperature in the range of from approximately 400° Centigrade to approximately 700° Centigrade.

8. The process of claim 7, wherein the catalyst of the first reaction step comprises copper chloride.

9. The process of claim 7, wherein the catalyst of the first reaction step comprises an admixture of copper chloride and a salt selected from the group consisting of potassium chloride, iron chloride, cesium chloride, zinc chloride, lead chloride, and bismuth chloride.

* * * * *

UNITED STATES PATENT AND TRADEMARK OFFICE
CERTIFICATE OF CORRECTION

PATENT NO.     : 6,545,191 B1                                    Page 1 of 1
DATED          : April 8, 2003
INVENTOR(S)    : Stauffer It is certified that error appears in the above-identified patent and that said Letters Patent is hereby corrected as shown below:

<u>Column 2,</u>
Line 57, please delete "=";

<u>Column 3,</u>
Line 58, after "product," please insert -- . --; and

<u>Column 4,</u>
Line 36, after "system," please insert -- . --.

Signed and Sealed this

Twelfth Day of August, 2003

JAMES E. ROGAN
*Director of the United States Patent and Trademark Office*